United States Patent [19]

Lobentanzer et al.

[11] Patent Number: 5,191,560
[45] Date of Patent: Mar. 2, 1993

[54] SOUND WAVE GENERATOR FOR THERAPEUTIC PURPOSES

[75] Inventors: Hans Lobentanzer; Norbert Wiesheu, both of Munich, Fed. Rep. of Germany

[73] Assignee: Dornier Medizintechnik GmbH, Fed. Rep. of Germany

[21] Appl. No.: 774,968

[22] Filed: Oct. 15, 1991

[30] Foreign Application Priority Data

Oct. 12, 1990 [DE] Fed. Rep. of Germany ....... 4032357

[51] Int. Cl.$^5$ ............................................. A61B 17/22
[52] U.S. Cl. .................................. 362/175; 367/142; 606/128; 128/24 EL
[58] Field of Search ................... 128/24 EL; 367/141, 367/142, 174, 175; 606/127, 128

[56] References Cited

U.S. PATENT DOCUMENTS

| | | | |
|---|---|---|---|
| 2,875,355 | 2/1959 | Petermann | 367/141 |
| 4,526,168 | 7/1985 | Hassler et al. | 128/24 EL |
| 4,622,969 | 11/1986 | Forssmann | 128/24 EL |
| 4,674,505 | 6/1987 | Pauli et al. | 128/24 EL |
| 4,766,888 | 8/1988 | Oppelt | 128/24 EL |
| 4,782,821 | 11/1988 | Reiter | 128/24 EL |
| 4,793,329 | 12/1988 | Mahler et al. | 128/24 EL |
| 4,796,608 | 1/1989 | Koehler | 128/24 EL |
| 4,834,074 | 5/1989 | Reichenberger | 128/24 EL |
| 4,834,106 | 5/1989 | Hassler et al. | 128/24 EL |
| 4,865,041 | 9/1989 | Hassler et al. | 128/24 EL |

FOREIGN PATENT DOCUMENTS

| | | | |
|---|---|---|---|
| 0421062 | 4/1991 | European Pat. Off. | 128/24 EL |
| 3505894 | 8/1986 | Fed. Rep. of Germany | 128/24 EL |
| 3624808 | 1/1988 | Fed. Rep. of Germany | 128/24 EL |
| 3739390 | 6/1989 | Fed. Rep. of Germany | 128/24 EL |
| 3742500 | 6/1989 | Fed. Rep. of Germany | 128/24 EL |

Primary Examiner—Stephen C. Pellegrino
Assistant Examiner—Glenn Dawson
Attorney, Agent, or Firm—Evenson, Wands, Edwards, Lenahan & McKeown

[57] ABSTRACT

This invention relates to a sound wave generator with a variable effective aperture angle according to the electromagnetic principle for therapeutic applications and particularly for the contactless smashing of a concrement situated in the body of a living being. The sound wave generator includes a flat coil and a metallic diaphragm which is insulated with respect to the flat coil. The flat coil includes three separately activatable and concentrically arranged coil sections. The sum of the areas of the inner coil section and the center coil section is equal to the sum of the areas of the central coil section and the outer coil section. By means of the varying activation of the coil sections, the aperture of the shock wave source can be changed so that the focus geometry and the peak pressures can be varied for different applications, particularly kidney and gallbladder lithotrity.

4 Claims, 2 Drawing Sheets

SOUND WAVE GENERATOR FOR THERAPEUTIC PURPOSES

BACKGROUND AND SUMMARY OF THE INVENTION

The invention relates to a sound wave generator for therapeutic applications such as the contactless smashing of a concrement situated in the body of a living being.

A device of the above-mentioned type is described in the European Patent Document EP 0 275 427. In front of a flat coil, an insulating foil is arranged and in front of the insulating foil, a diaphragm is arranged which is made of an electrically conductive material. By the feeding of a discharge current to the flat coil, that is, by electrical primary energy, the diaphragm is abruptly moved away from the flat coil and generates plane waves in a liquid medium bordering on the diaphragm which propagate perpendicularly to the diaphragm surface and are focussed by means of an arrangement of acoustic focussing lenses.

The German patent Document DE 37 39 390 A1 describes a shock wave source with a flat coil and a diaphragm which is insulated with respect to it, the flat coil consisting of two coil sections which can be activated separately and/or jointly.

In the German Patent Document DE 33 08 637 A1, an ultrasonic apparatus is described which comprises several concentrically arranged ring-shaped ultrasonic emitters, each ultrasonic emitter having the same area.

In the German Patent Document DE 34 17 985 A1, a shock wave generator is described by means of which a focal point can be generated with a clearly increased propagation in the axial direction.

For different applications, for example, for kidney or gallbladder lithotrity, different requirements exist with respect to the focus geometry and the peak pressure.

Because of the problems concerning damage to the tissue, a laterally wider focus (FWHM (Full Width at Half Maximum)=6-10 mm) with peak pressures of approximately 500 bar is desirable. Such values are typically generated by means of sound wave generators of small aperture angles (50°-60°). The comparatively long axial focus (50-100 mm) may be accepted in the case of kidney lithotrity.

For gallbladder lithotrity, on the other hand, a laterally narrower focus (FWHM=3-5 mm) with peak pressures of approximately 800 bar is desirable, in which case the axial half-width value should be at approximately 40 mm, since sensitive structures (liver, lungs, kidneys, spinal column) are situated in front of and behind the gallbladder. Such values are typically achieved by means of shock wave sources of high aperture angles (80°-90°).

It is an object of the invention to provide a sound wave generator of the initially mentioned type which can be adapted to the different applications.

According to the invention, this object is achieved by providing a sound wave generator with a variable effective aperture angle according to the electromagnetic principle for therapeutic applications and particularly for the contactless smashing of a concrement situated in the body of a living being, comprising:
a flat coil arrangement, and
a metallic diaphragm insulated with respect to the flat coil arrangement,
wherein the flat coil arrangement includes an inner coil section, a central coil section concentrically surrounding the inner coil section, and an outer coil section concentrically surrounding the central coil section,
and wherein the electric circuit control apparatus includes means operable to selectively actuate respective different pairs of said coil sections to thereby accommodate use of the sound wave generator with respective different effective aperture angles.

By means of the invention, it is achieved that, by changing the effective aperture angle, the sound wave generator can by optimally used for different therapeutic applications, such as kidney and gallbladder lithotrity. When the plane sound field has a width of D, and the focussing lens system has a focal distance of f, the effective aperture angle is the value $$2 \cdot \arctan(D/2f).$$

This corresponds to the definition of the aperture angle which is used in optics where the adjective "effective" indicates that a sound-wave-free space may exist between the peripheral rays of the sound field, as in FIG. 2b.

Other objects, advantages and novel features of the present invention will become apparent from the following detailed description of the invention when considered in conjunction with the accompanying drawings.

DETAILED DESCRIPTION OF THE DRAWINGS

Figure 1:
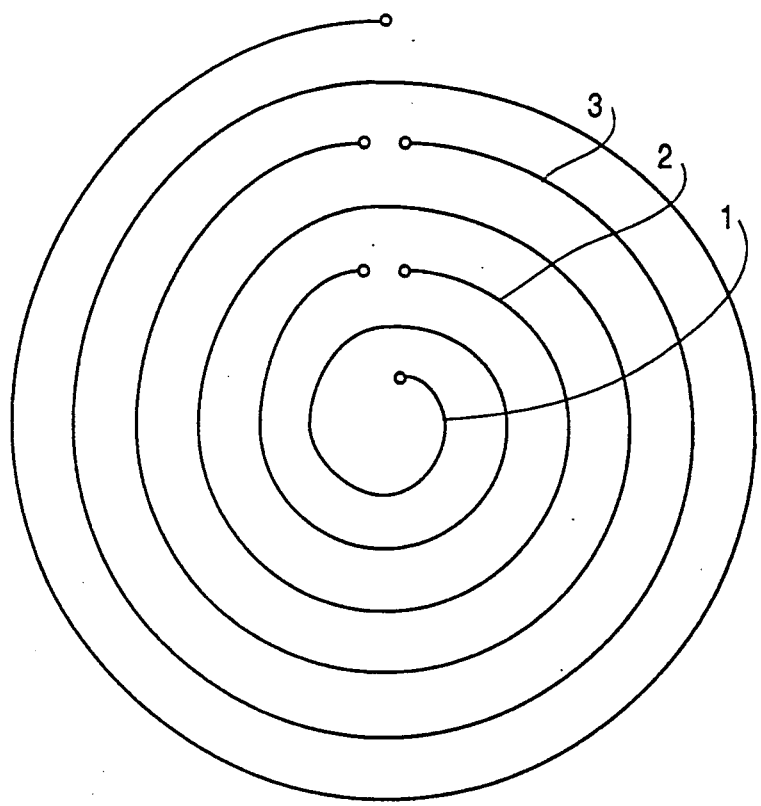
FIG. 1 is an outlined top schematic view of a flat coil of three concentrically arranged coil sections.

FIG. 1 is a schematic top view of a flat coil which comprises three concentrically arranged coil sections 1, 2, 3 (for reasons of clarity, only a few wound coils are shown for each coil section). Each of the three coil sections can be separately supplied with current with a single power supply by means known to those skilled in the art.

Figure 2A:
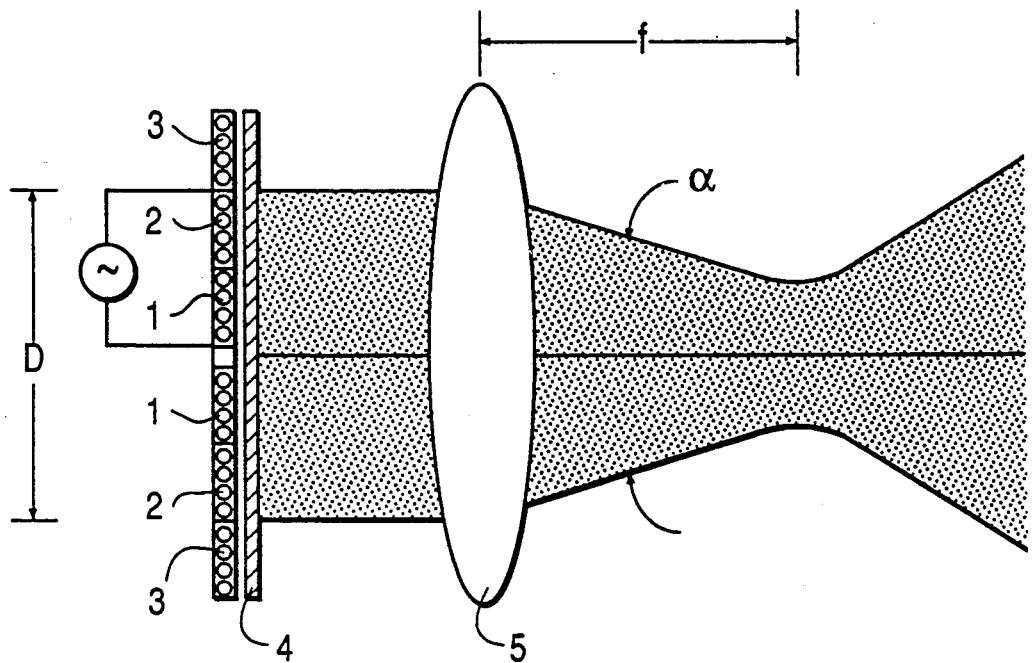
FIGS. 2a and 2b are respective schematic views depicting two operational arrangements by means of which different focus geometries and peak pressures are achieved, according to preferred embodiments of the invention.
Figure 2B:
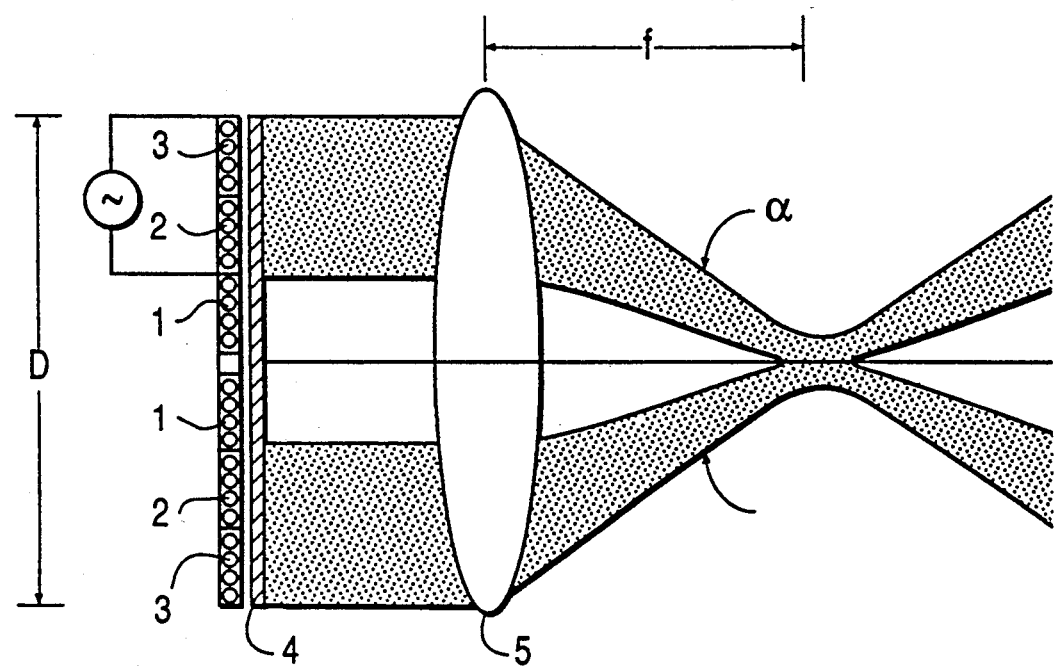

FIGS. 2a and 2b illustrate how the focus geometry and peak pressures can be varied by two different wirings of the three concentric coil sections 1, 2, 3. The cross-sectional areas of the wound coils which are part of the same coil section are separated from the others by divisions in the drawing FIGS. 2a and 2b. In this schematic representation, it should be noted that the ratio of sizes of the coil areas of the coil sections are not depicted with the sum of the areas of the coil sections 1 and 2 being equal to the sum of the areas of the coil sections 2 and 3. However, in certain preferred embodiments those sums are equal. In this case and in the following, the coil area is understood to be only the area taken up by the wound coils in the case of a section extending perpendicularly with respect to the coil axis. The coil area is the radiation surface area. The shown arrangement is rotationally symmetrical with respect to the coil axis. The aperture angle $\alpha$ is shown on FIGS. 2a and 2b.

In FIG. 2a, the discharge current flows only through the inner and central coil section 1, 2. For this purpose, the two coils may, for example, be connected in series or one discharge pulse respectively is fed to each of the two coil sections. By means of the deflecting of the diaphragm 4, a cylindrical plane wave front is generated, the diameter of which corresponds essentially to that of coil section 2. The wave front is focussed in a focussing lens 5. In an embodiment of the invention, the aperture angle is between 50 and 70 degrees.

In FIG. 2b, on the other hand, the discharge current flows through the central and the outer coil section 2, 3. The deflection of the diaphragm 4 results in a tube-shaped plane wave front with an area which essentially corresponds to the coil areas of the coil sections 2, 3 through which the current flows. On the basis of the larger effective aperture angle in the sense of the above-mentioned definition, in the case of the arrangement according to FIG. 2a, an axially as well as laterally wider focus at lower peak pressures is obtained than in the case of the arrangement according to FIG. 2b. It is also well known in the art to use electronic gates or switches to selectively operate different circuits or devices. This allows different pairs of coil sections to be energized by the respective electronic control device without the need for independently hooking up the respective coils each time a new pair was to be energized together.

It is particularly advantageous that, in the two shown arrangements, despite the different effective aperture angles, the position of the focus is not changed. The electromagnetic coupling between the coil and the diaphragm (one measure in this regard is, for example, the leakage inductance) is, among others, a function of the size of the coil area through which the current flows. For this reason, particularly also the ratios of sizes of the coil section areas with respect to one another are significant.

Figure 3:
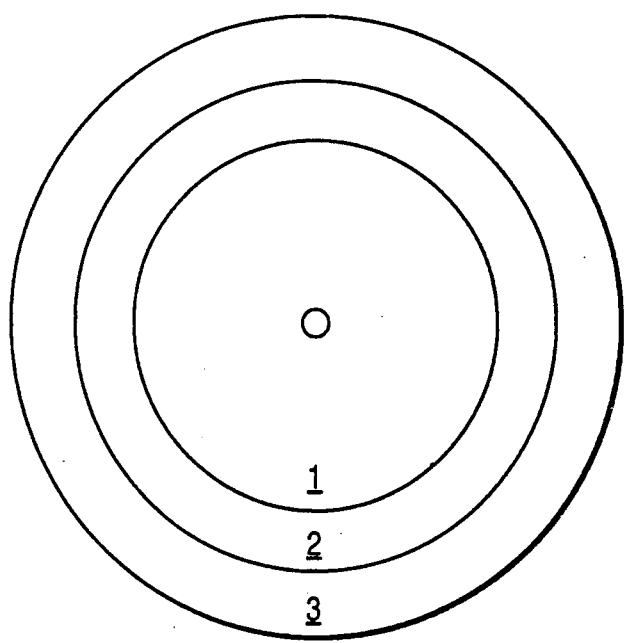
FIG. 3 is a top schematic view of a flat coil, constructed according to a preferred embodiment of the invention.

A preferred embodiment in this respect is shown in FIG. 3. A flat coil is illustrated there which comprises three concentrically arranged coil sections 1, 2, 3. In this case, the coil areas of the three coil sections are selected in such a manner that the sum of the coil area of the inner coil I and of the central coil 2 is equal to the sum of the coil area of the central coil 2 and the outer coil 3. By means of the selection of the ratio of sizes, it is achieved that the whole coil area through which the current flows, in the case of the current passage through the inner and central coil section 1, 2 (for example, in kidney lithotrity), is just as large as in the case of the current passage through the central and outer coil section 2, 3 (for example, in gallbladder lithotrity).

In addition, an arrangement of the coil sections is possible in which, while the wiring of the coil sections differs but the electric primary energy is the same, the same acoustic energy is radiated.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. A sound wave generator with a variable effective aperture angle according to the electromagnetic principle for therapeutic applications and particularly for the contactless smashing of a concrement situated in the body of a living being, comprising:
   a flat coil arrangement,
   a metallic diaphragm insulated with respect to the flat coil arrangement, a device for focusing sound waves produced by said diaphragm, and
   an electric circuit control apparatus, electrically connected to the flat coil arrangement, for controlling actuation of the flat coil arrangement,
   wherein the flat coil arrangement includes an inner coil section, a central coil section concentrically surrounding the inner coil section, and an outer coil section concentrically surrounding the central coil section, each of said sections having a given area,
   and wherein the electric circuit control apparatus includes means operable to selectively actuate respective different pairs of said coil sections to cooperate with said device for focusing to produce respective different effective aperture angles.

2. A sound wave generator according to claim 1, wherein the sum of the areas of the inner coil section and the central coil section is substantially equal to the sum of the areas of the central coil section and the outer coil section.

3. A sound wave generator according to claim 1, wherein a low effective aperture angle of between 50°–70° is obtained by means of the simultaneous actuation of the inner coil section and central coil section, and wherein a higher effective aperture angle of between 70°–100° is obtained by means of the simultaneous activating of the central coil section and the outer coil section.

4. A sound wave generator according to claim 2, wherein a low effective aperture angle of between 50°–70° is obtained by means of the simultaneous activating of the inner coil section and central coil section, and wherein a higher effective aperture angle of between 70°–100° is obtained by means of the simultaneous actuation of the central coil section and the outer coil section.

* * * * *